(12) United States Patent
Alshemari

(10) Patent No.: US 8,608,774 B1
(45) Date of Patent: Dec. 17, 2013

(54) BIFURCATED FORCEPS

(71) Applicant: Hasan M. Sh. Sh. Alshemari, Saad Al Abdulla (KW)

(72) Inventor: Hasan M. Sh. Sh. Alshemari, Saad Al Abdulla (KW)

(*) Notice: Subject to any disclaimer, the term of this patent is extended or adjusted under 35 U.S.C. 154(b) by 0 days.

(21) Appl. No.: 13/761,063

(22) Filed: Feb. 6, 2013

Related U.S. Application Data

(63) Continuation of application No. 13/633,783, filed on Oct. 2, 2012, now abandoned.

(51) Int. Cl.
*A61B 17/50* (2006.01)

(52) U.S. Cl.
USPC .......................................... 606/210

(58) Field of Classification Search
USPC .................. 606/205–208, 210, 211; 294/99.2
See application file for complete search history.

(56) References Cited

U.S. PATENT DOCUMENTS

| | | | |
|---|---|---|---|
| 2,665,692 A | | 1/1954 | L'Esperance |
| 4,610,252 A | * | 9/1986 | Catalano ...................... 606/157 |
| 4,938,214 A | * | 7/1990 | Specht et al. ................ 606/174 |
| 5,178,622 A | * | 1/1993 | Lehner, II ................... 606/107 |
| 5,217,464 A | | 6/1993 | McDonald |
| D341,886 S | | 11/1993 | Stolte |
| 5,613,499 A | | 3/1997 | Palmer et al. |
| 5,997,567 A | | 12/1999 | Cangelosi |
| 6,776,615 B2 | | 8/2004 | Dietrich |
| D625,008 S | | 10/2010 | Boedeker |
| 2005/0255421 A1 | | 11/2005 | Michaelson |

FOREIGN PATENT DOCUMENTS

| | | |
|---|---|---|
| GB | 2933047 | 6/2007 |
| WO | WO 2004/064871 | 8/2004 |

* cited by examiner

*Primary Examiner* — Thomas McEvoy
(74) *Attorney, Agent, or Firm* — Richard C. Litman

(57) ABSTRACT

The bifurcated forceps is a tweezers-like instrument having two elongate, flattened arms joined at their mutual proximal ends, and each arm extends to a distal end having two laterally separated tines extending therefrom. The mutually facing surfaces of the corresponding tines of each arm are provided with serrations or teeth along the majority of their lengths, the facing serrations meshing with one another. The bifurcated forceps may have laterally straight arms, or laterally curved arms. Reusable forceps may be formed of surgical steel, and disposable forceps may be formed of a suitable plastic. The laterally separated tines enable the bifurcated forceps to grip a portion of tissue or other matter simultaneously at two separate points, thereby holding a greater span of the tissue clear of the underlying structure to facilitate surgical procedures and the like.

6 Claims, 5 Drawing Sheets

BIFURCATED FORCEPS

CROSS-REFERENCE TO RELATED APPLICATIONS

This is a continuation of my prior application Ser. No. 13/633,783, filed Oct. 2, 2012 now pending.

BACKGROUND OF THE INVENTION

1. Field of the Invention

The present invention relates generally to surgical implements, and particularly to bifurcated forceps in which each of the jaws has two parallel, laterally separated tines for gripping a sheet of material (anatomic tissue, etc.) simultaneously at two spaced apart locations.

2. Description of the Related Art

The medical profession requires a number of specialized instruments for various medical procedures. It is often necessary to retract or otherwise displace some tissue structure (e.g., skin, subcutaneous structure, blood vein or artery, etc.) in order to access some underlying organ or other structure of concern. Some form of gripping device, e.g., forceps or tweezers, is customarily used for such purpose.

The problem with conventional forceps and tweezers is that they have only two mutually opposed jaws, which each comprise a single element. Hence, the tissue structure can only be gripped at one point between the two jaws. As most bodily tissues are relatively soft and flaccid, particularly when the patient is anesthetized, the tissue tends to withdraw back toward its original position or location. The underlying structure is therefore exposed only in a relatively narrow area beneath the point gripped by the conventional forceps, which may not provide the surgeon with sufficient line of sight to observe as required and/or sufficient room to perform the procedure. Accordingly, two sets of conventional forceps or tweezers are commonly used. An assistant (operating room nurse, etc.) holds the second set in response to the directions from the surgeon. Clearly, this is not only a labor intensive procedure, but it also often results in interfering with the line of sight and the work of the surgeon, even though it is necessary to open up the sightline and operating path for the surgeon.

Thus, a bifurcated forceps solving the aforementioned problems is desired.

SUMMARY OF THE INVENTION

The bifurcated forceps has two mutually opposed jaws, each jaw having two laterally spaced tines. Corresponding tines of each jaw are aligned with one another to grip an article therebetween when the forceps are closed. The spaced apart tines result in the article being gripped simultaneously at two spaced apart locations, thus spreading the article more widely for better access to the underlying tissue or other structure.

The tines preferably include a plurality of teeth or serrations thereon to preclude or reduce slippage of any tissue gripped therebetween. The forceps are preferably in the form of two resilient arms formed of flat material. The proximal ends of the forceps are permanently joined to one another, and their distal ends normally are spread until resiliently closed by the operator. Corrosion-resistant surgical grade steel, i.e., "stainless" steel, may be used for reusable forceps, and plastic is the material of choice for disposable forceps. The spacing between the tines of each jaw may be adjusted as desired, and the flat arms may include lateral offsets.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The bifurcated forceps has two mutually opposed jaws, each of the jaws having two laterally separated gripping tines extending therefrom. This configuration provides for the simultaneous gripping of tissue at two laterally separated points, thereby facilitating surgical operations and procedures and reducing or obviating the need for an assistant to manipulate a second pair of forceps.

Figure 1:
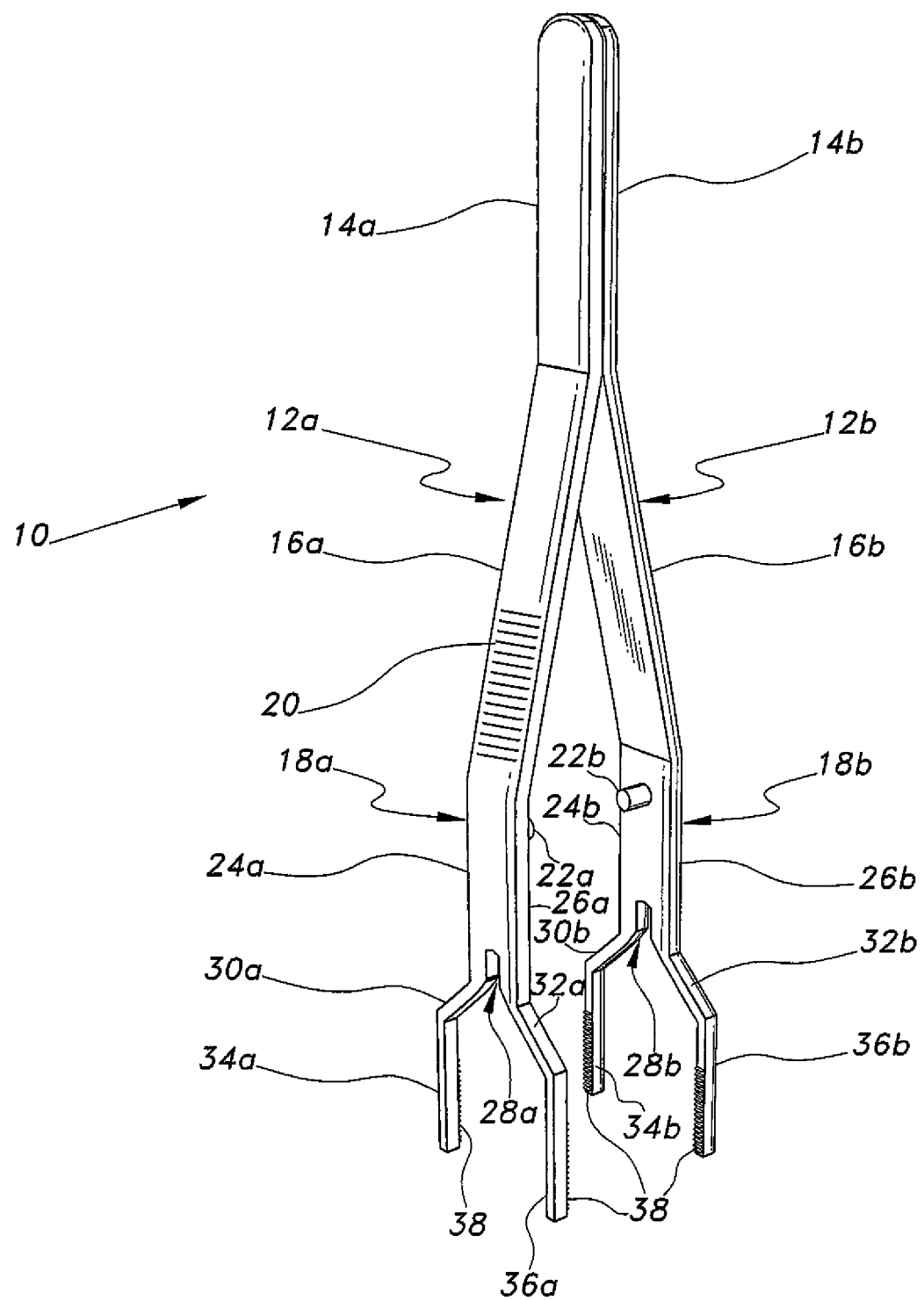
FIG. 1 is a detailed perspective view of bifurcated forceps according to the present invention, illustrating its various features.
Figure 2:
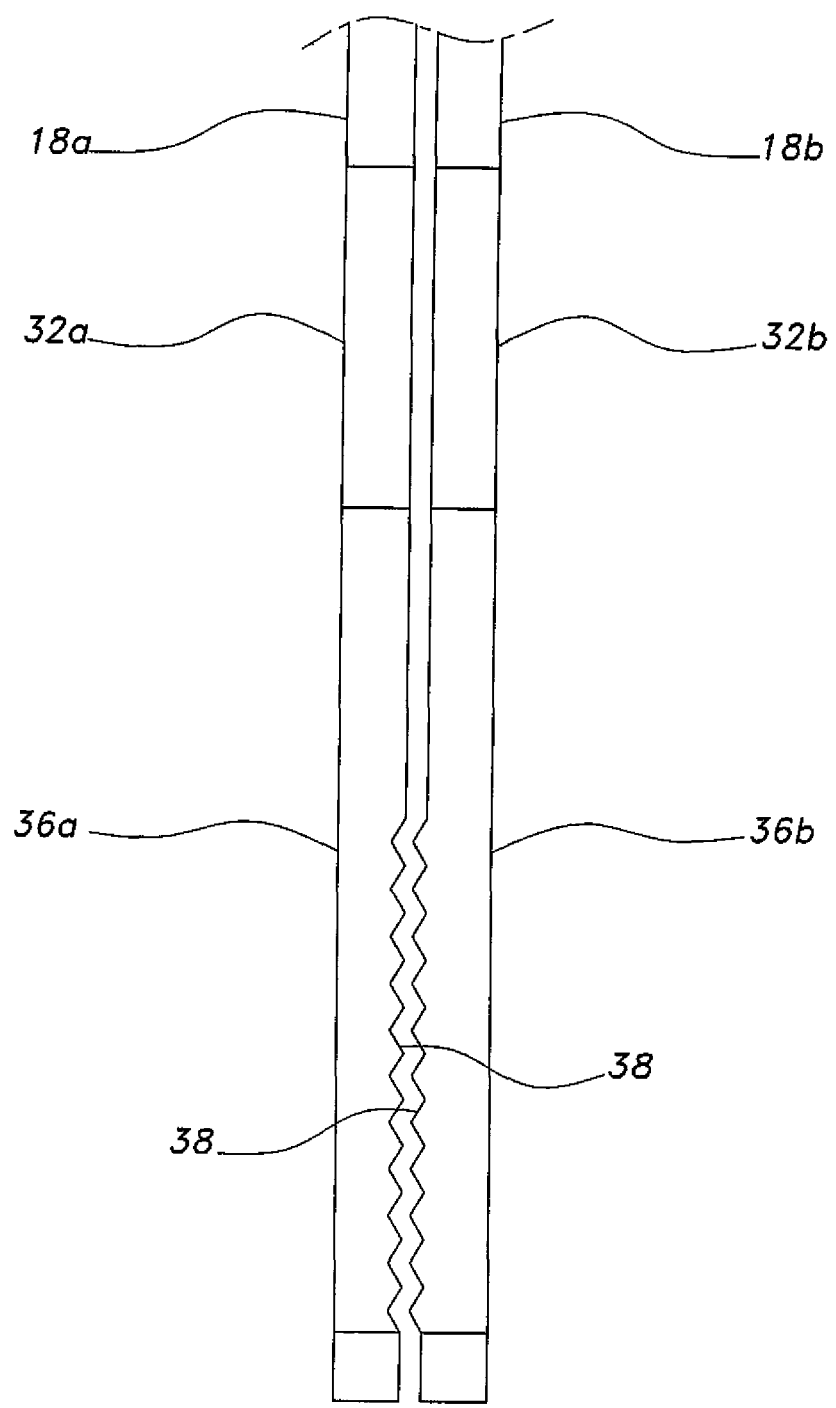
FIG. 2 is a partial side elevation view of the jaw portion of the bifurcated forceps of FIG. 1, illustrating the meshing or interlocking of the mutually facing teeth or serrations of the two mutually opposed jaw tines.
Figure 3:
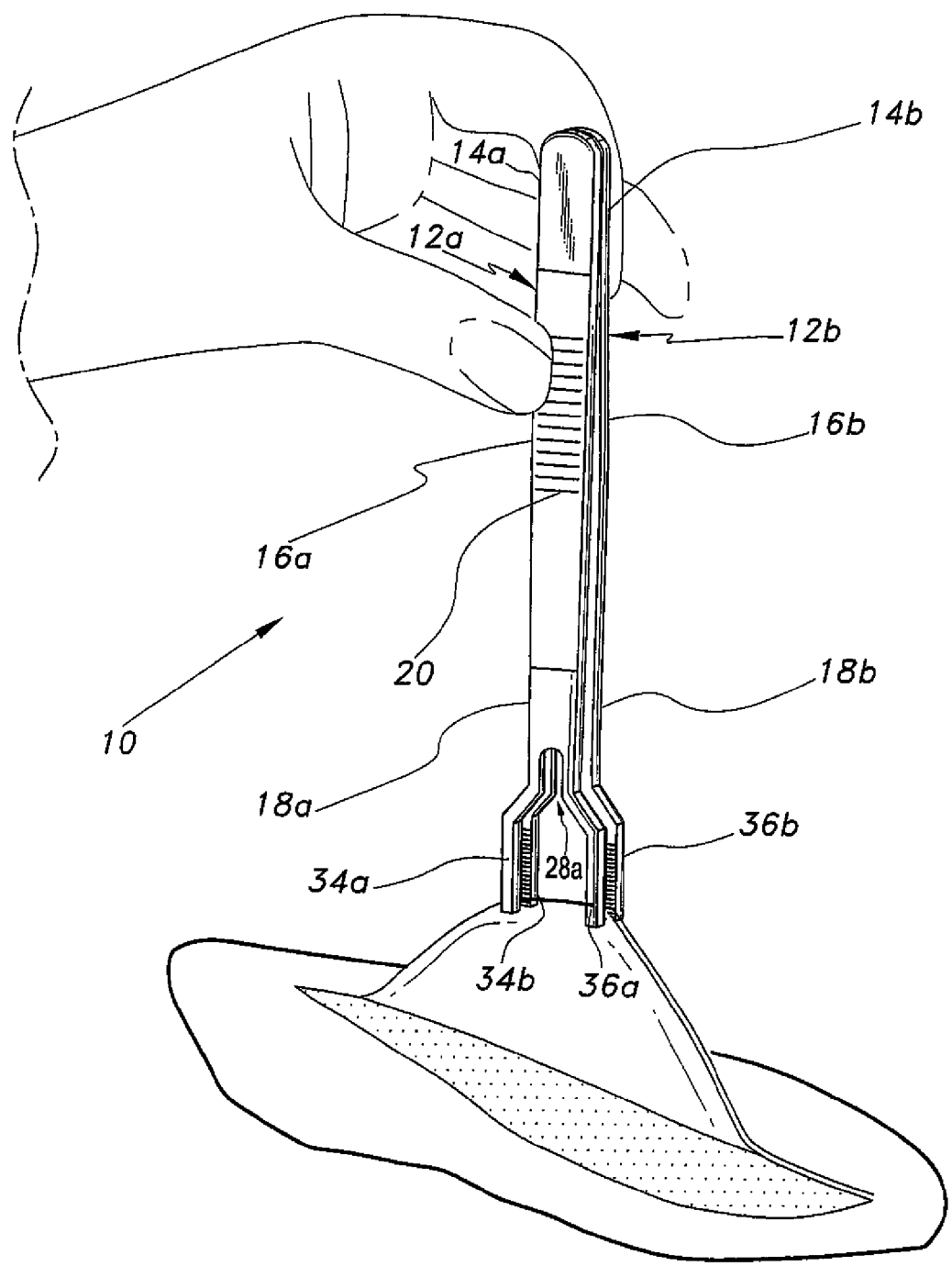
FIG. 3 is an environmental perspective view of the bifurcated forceps of FIG. 1, showing their use in a surgical procedure.

FIG. 1 of the drawings provides an illustration of a first embodiment 10 of the bifurcated forceps, FIG. 2 illustrates details of the two opposed tines and their interlocking teeth or serrations, and FIG. 3 provides an environmental perspective view of the forceps 10 in use. The bifurcated forceps 10 comprises mutually opposed first and second anus 12a and 12b, which are mirror images of one another. Each of the arms 12a, 12b is formed of an elongate, wide, relatively thin, flexible sheet of material having a flat proximal end portion 14a and 14b, the two proximal end portions 14a, 14b being permanently joined to one another along the entire lengths of the proximal portions, e.g., by welding where a reusable forceps is formed of surgical steel or bonding where a disposable material, such as plastic, is used to form the bifurcated forceps 10. The arms 12a, 12b may be squeezed or flexed towards each other, and resiliently return to their original position when released.

Each of the arms 12a, 12b further includes an intermediate portion 16a, 16b that extends from its respective proximal portion 14a, 14b. The two intermediate portions 16a, 16b spread or diverge from one another from their juncture with their proximal portions 14a, 14b to their junctures with the respective distal portions 18a, 18b of the arms that extend from the intermediate portions 16a, 16b. Each of the two intermediate portions 16a, 16b includes a textured grip area 20 disposed thereon, one of the grip areas 20 being shown on the arm 12a in FIGS. 1 and 3. The opposite grip area is not visible in the drawings, but it will be understood that both of the intermediate areas 16a and 16b include such textured grip areas 20 due to their mirror image configurations.

The two distal portions 18a, 18b of the bifurcated forceps 10 are spaced apart from and parallel to one another when the forceps 10 is in its relaxed, uncompressed state. A closure limit stop, respectively 22a and 22b, extends inwardly from each distal portion 18a and 18b, adjacent its juncture with the corresponding intermediate portion 16a, 16b of the forceps 10. The two inwardly disposed, mutually facing closure limit stops 22a, 22b contact one another when the intermediate portions 16a, 16b of the forceps 10 are squeezed toward one another to limit the force that may be applied by the tines on tissue during use.

Each distal portion 18a, 18b has two mutually laterally opposed sides or edges. The first distal portion 18a has edges or sides 24a and 26a, and the opposite second distal portion 18b has edges or sides 24b and 26b. The two opposite sides 24a and 26a of the first distal portion 18a define a slot 28a therebetween opposite the juncture of the distal portion 18a with the intermediate portion 16a. The opposite sides 24b, 26b define a corresponding slot 28b therebetween. It will be seen that the corresponding sides or edges 24a, 24b are directly opposite one another, and the corresponding sides or edges 26a, 26b are also directly opposite one another.

First and second angular extensions, respectively 30a and 32a, extend laterally outward and distally from the end of the first distal portion 18a of the arm 12a, extending from points adjacent the slot 28a. Corresponding angular extensions 30b and 32b extend laterally outward and distally from the end of the second distal portion 18b, from points adjacent the slot 28b. The angular extensions 30a, 32a, 30b, 32b are substantially linear, and extend at an obtuse angle from the corresponding sides 24a, 26a, 24b, 26b of the arms 12a, 12b. An elongate tine extends from the distal end of each of the extensions 30a, 32a. A first tine 34a extends from the first side extension 30a, a second tine 36a extends from the second side extension 32a, a corresponding first tine 34b extends from the first side extension 30b, and a corresponding second tine 36b extends from the second side extension 32b. The two tines 34a and 36a of the first distal portion 18a are spaced apart from and parallel to one another, and the two tines 34b, 36b of the second distal portion 18b are likewise spaced apart from and parallel to one another. The tines 34a, 36a, 34b, 36b extend substantially parallel to the sides 24a, 26a, 24b, 26b of the arms 12a, 12b.

The mutually facing gripping surfaces of the corresponding tines, i.e., first tines 34a and 34b and second tines 36a and 36b, each have a plurality of serrations or teeth 38 disposed thereon along the majority of their lengths. FIG. 2 provides a detailed view of these serrations or teeth 38. It will be seen in FIG. 2 that the teeth or serrations 38 are oriented laterally across the width of each of the tines 34a-34b and 36a-36b, i.e., their crests and their troughs extend laterally across the tines 34a-34b and 36a-36b. This configuration greatly reduces the possibility that tissue or other material gripped between opposing tines 34a, 34b and 36a, 36b will retract or slip longitudinally along the length of the tines 34a-34b and 36a-36b. It will also be seen that the mutually opposed teeth or serrations 38 of each of the tines, e.g., tines 36a, 36b as shown in FIG. 2, mesh or interlock with one another, with the crests of the serrations 38 of the tine 36a being directly opposite and facing the valleys or troughs of the opposite serrations 38 of the tine 36b, and vice versa. This configuration increases the contact area of the opposed serrations 38, and thus the contact area upon any material gripped therebetween.

Figure 4:
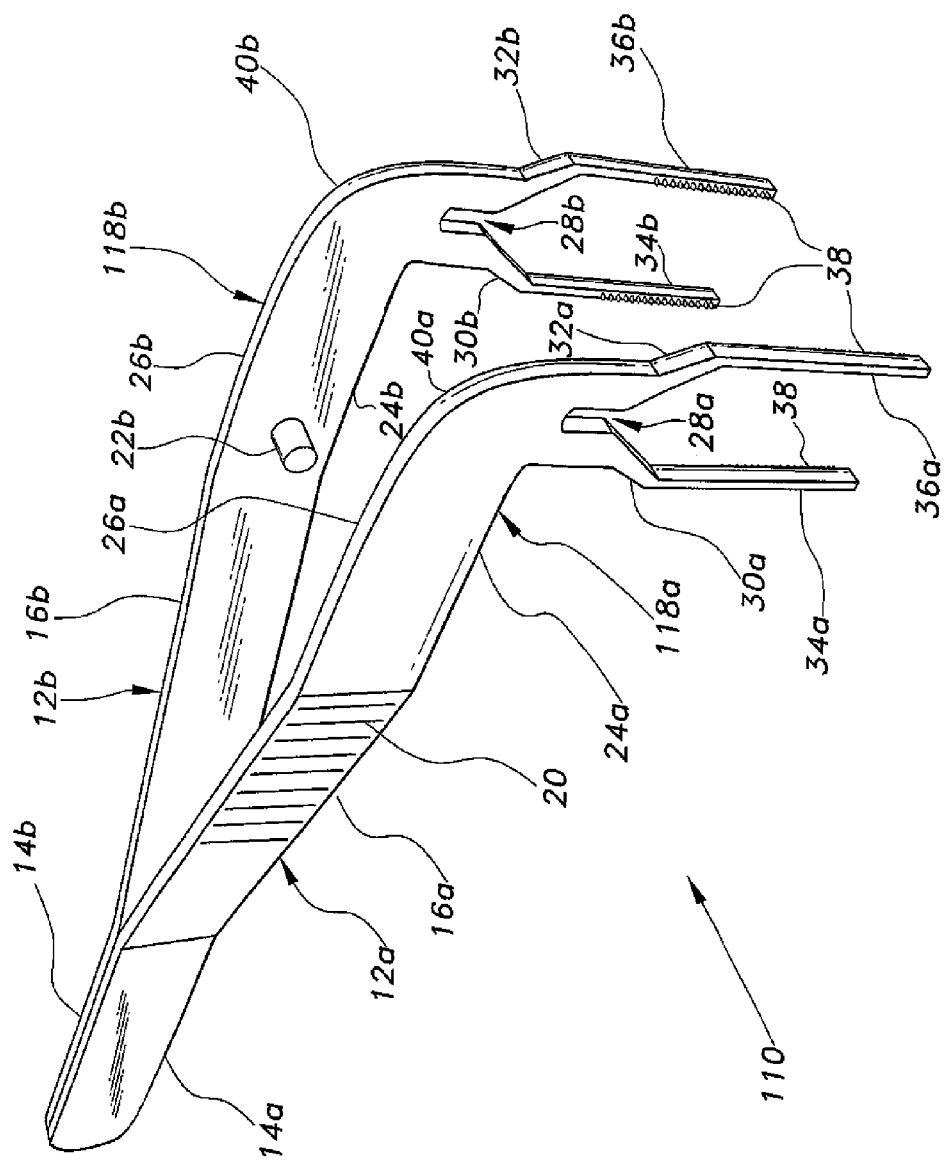
FIG. 4 is a detailed perspective view of a second embodiment of bifurcated forceps according to the present invention, having laterally offset distal arms and jaws.

FIG. 4 of the drawings provides a perspective view of a second embodiment of the bifurcated forceps, designated as bifurcated forceps or forceps 110. The forceps 110 incorporate most of the structure and features of the forceps 10 of FIGS. 1 through 3, i.e., mutually opposed first and second arms 12a and 12b having flat proximal end portions 14a, 14b permanently joined and immovably affixed to one another, intermediate portions 16a, 16b extending and diverging from their respective proximal portions 12a, 12b, textured grip areas 20 disposed on the arms 12a, 12b, and mutually parallel distal portions 118a, 118b extending from their respective intermediate portions 16a, 16b.

The distal portions 118a and 118b differ from the corresponding distal portions 18a and 18b of the forceps 10 of FIGS. 1 and 3, in that each of the distal portions 118a and 118b has a lateral bend or curvature, respectively 40a and 40b, therein. The bends 40a and 40b are coplanar with the widths of their respective distal arm portions 118a and 118b and the planes defined by their respective edges 24a, 26a and tines 34a, 36a (for the first distal arm portion 118a) and edges 24b, 26b and tines 34b, 36b (for the second distal arm portion 118b). The bends 40a and 40b may be on the order of 90°, generally as shown in FIG. 4, or any other desired offset angle.

Each of the distal portions 118a, 118b may include a closure limit stop extending inwardly therefrom, stop 22b being visible in FIG. 4. The tine extension ends of the distal portions 118a, 118b define respective slots 28a and 28b therebetween and include first and second angular extensions 30a, 32a for the first distal portion 118a and extensions 30b, 32b for the second distal portion 118b, similar to the tine extension ends 30a-32a and 30b-32b of the forceps 10 of FIGS. 1-3. Tines 34a and 36a extend from the first and second extensions 30a and 32a of the first distal portion 118a, and tines 34b and 36b extend from the first and second extensions 30b and 32b of the second distal portion 118b, similar to the configuration of the forceps 10. The mutually facing gripping surfaces of the corresponding tines have a plurality of laterally oriented and meshing or interlocking serrations or teeth 38 disposed thereon along the majority of their lengths, as provided for the forceps 10 and shown in detail in FIG. 2.

Figure 5:
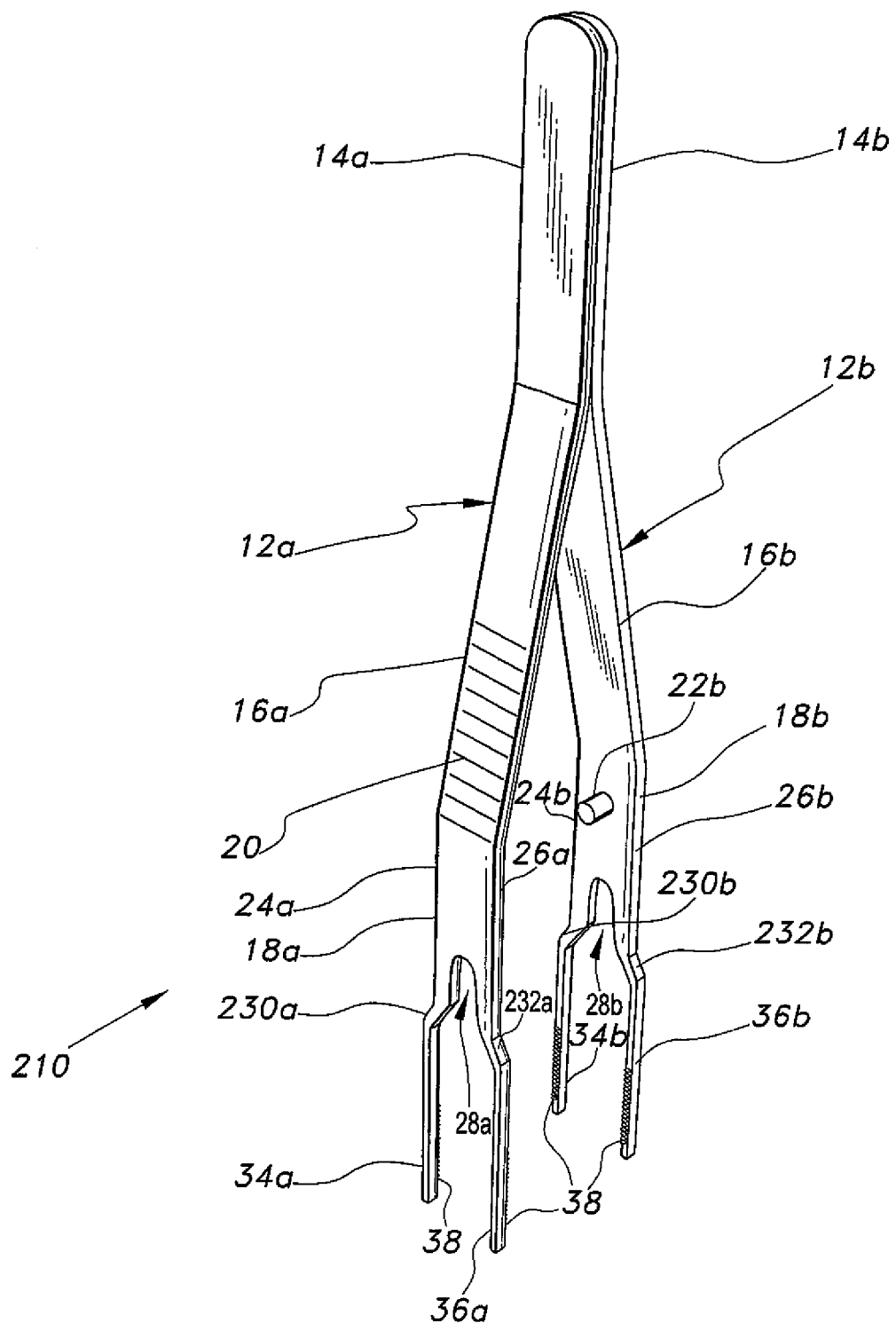
FIG. 5 is a detailed perspective view of a third embodiment of bifurcated forceps according to the present invention, having a narrower spacing between the two laterally spaced tines of each jaw than is the case with the first embodiment bifurcated forceps.

FIG. 5 is a perspective view of another alternative embodiment, designated as bifurcated forceps or forceps 210. The forceps 210 is quite similar to the forceps 10 of FIGS. 1-3, having mutually opposed first and second arms 12a and 12b having flat proximal end portions 14a and 14b permanently joined and immovably affixed to one another, intermediate portions 16a and 16b extending and diverging from their respective proximal portions 12a, 12b, textured grip areas 20, and mutually parallel distal portions 18a and 18b extending from their respective intermediate portions 16a, 16b.

Each of the distal portions 18a, 18b may include a closure limit stop extending inwardly therefrom, stop 22b being visible in FIG. 5. The tine extension ends of the distal portions 18a, 18b define respective slots 28a and 28b therebetween and include first and second angular extensions 230a, 232a of the first distal portion 18a and extensions 230b, 232b of the second distal portion 18b, as in the tine extension ends of the forceps 10 of FIGS. 1-3. Tines 34a and 36a extend from the first and second extensions 230a and 232a of the first distal portion 18a, and tines 34b and 36b extend from the first and second extensions 230b and 232b of the second distal portion 18b, similar to the configuration of the forceps 10. The mutually facing gripping surfaces of the corresponding tines 34a-36a, 34b-36b have a plurality of laterally oriented and meshing or interlocking serrations or teeth 38 disposed thereon along the majority of their lengths, as provided for the forceps 10 shown in FIG. 2.

However, it will be seen that the angular extensions 230a, 232a, 230b, and 232b are somewhat shorter than their counterpart extensions of the embodiments 10 and 110 of FIGS. 1 through 4. This results in the lateral spacing between corresponding tines 34*a*, 36*a* and 34*b*, 36*b* being somewhat narrower for the embodiment 210 of FIG. 5 than for the embodiments 10 and 110 of FIGS. 1 through 4. This is the only substantial difference between the forceps 210 of FIG. 5 and the forceps 10 and 110 of FIGS. 1 through 4. It will be seen that the lateral spacing between corresponding tines may be made to any practicable width. Accordingly, the bifurcated forceps greatly facilitate the elevation of tissue to facilitate access to the underlying anatomical tissue during medical operations and procedures.

It is to be understood that the present invention is not limited to the embodiments described above, but encompasses any and all embodiments within the scope of the following claims.

I claim:

1. A bifurcated forceps, comprising:

mutually opposed first and second arms, each of the arms being an elongate, wide, thin, flexible sheet of material having a proximal end portion permanently affixed to the proximal end portion of the opposite arm along the entirety of the proximal end portions, the arms being compressible towards each other and resiliently returning to their original position when released, each of the arms further having an intermediate portion and a distal portion, wherein the intermediate portions of each of the arms diverge angularly from one another from their mutually attached proximal end portions toward their distal portions and the distal portions of each of the arms are spaced apart from one another and parallel to one another throughout their entire length;

each of the distal portions having:

a first side and a second side opposite the first side, the first side and the second side of the distal portions defining a slot therebetween;

an elongate first tine extending from the first side of each of the distal portions;

an elongate second tine extending from the second side of each of the distal portions, the second tines being separated laterally from the corresponding first tines so that each of the distal portions has a pair of tines, the pairs of tines having mutually facing gripping surfaces having a plurality of serrations extending laterally across the tines, the serrations being disposed along the majority of the length of each of the tines;

whereby the forceps is adapted for simultaneously gripping an elongate object at two different locations between the two pairs of spaced apart tines.

2. The bifurcated forceps according to claim 1, wherein each of the arms has a lateral bend disposed along the distal portion thereof.

3. The bifurcated forceps according to claim 1, further comprising a textured grip area disposed upon the intermediate portion of each of the arms.

4. The bifurcated forceps according to claim 1, further comprising mutually facing first and second closure limit stops disposed respectively upon the distal portion of each of the arms.

5. The bifurcated forceps according to claim 1, wherein the arms are formed of surgical steel.

6. The bifurcated forceps according to claim 1, wherein the arms are formed of plastic material.

\* \* \* \* \*